▶ 43 ▶ 39

United States Patent [19]
Kamahori et al.

[11] Patent Number: 5,458,761
[45] Date of Patent: Oct. 17, 1995

[54] METHOD FOR ANALYZING NUCLEIC ACID OR PROTEIN AND APPARATUS THEREFOR

[75] Inventors: Masao Kamahori; Takeshi Fujita, both of Hatoyama; Shinichiro Umemura, Hachiohji; Takashi Yamada, Hatoyama, all of Japan

[73] Assignee: Hitachi, Ltd., Tokyo, Japan

[21] Appl. No.: 378,973

[22] Filed: Jan. 27, 1995

Related U.S. Application Data

[62] Division of Ser. No. 111,508, Aug. 24, 1993, Pat. No. 5,409,586.

[30] Foreign Application Priority Data

| Aug. 26, 1992 | [JP] | Japan | 4-226894 |
| Oct. 26, 1992 | [JP] | Japan | 4-287264 |
| Oct. 29, 1992 | [JP] | Japan | 4-291161 |
| Jan. 21, 1993 | [JP] | Japan | 5-008151 |

[51] Int. Cl.$^6$ .......................... G01N 27/26; G01N 27/447
[52] U.S. Cl. .................. 204/299 R; 204/182.8; 204/180.1
[58] Field of Search ...................... 204/299 R, 182.8, 204/180.1

[56] References Cited

U.S. PATENT DOCUMENTS

| 3,847,785 | 11/1974 | Allington | 204/299 R |
| 4,810,456 | 3/1989 | Bente, III et al. | 264/510 |
| 4,859,301 | 8/1989 | Brenner et al. | 204/180.1 |
| 4,898,658 | 2/1990 | Karger et al. | 204/299 R |
| 5,085,756 | 2/1992 | Swedberg | 204/299 R |
| 5,085,757 | 2/1992 | Karger et al. | 204/299 R |
| 5,110,424 | 5/1992 | Chin | 204/180.1 |
| 5,240,576 | 8/1993 | Lauer et al. | 204/299 R |

OTHER PUBLICATIONS

Ewald J. B. M. Mensink et al "Detection of point mutations in DNA using capillary electrophoresis in a polymer network" Journal of Chromatography, vol. 621, No. 2 (24 Nov. 1993) 149–156.

Takashi Satow et al "Simultaneous determination of the migration coefficient of each base in heterogeneous oligo–DNA by gel filled capillary electrophoresis" Journal of Chromatography A, vol. 652, No. 1 (15 Oct. 1993) 23–30.

Science, vol. 222, Oct. 1983, pp. 266–272. James W. Jorgenson et al "Capillary Zone Electrophoresis".

Analytical Chemistry, May 1990, 62, pp. 900–903, Lloyd M. Smith et al " High Speed Separations of DNA Sequencing Reactions by Capillary Electrophoresis".

(List continued on next page.)

Primary Examiner—John Niebling
Assistant Examiner—John S. Starsiak, Jr.
Attorney, Agent, or Firm—Fay, Sharpe, Beall, Fagan, Minnich & McKee

[57] ABSTRACT

Analysis of a nucleic acid samples having thousands of bases is conducted by capillary electrophoresis. The electrophoretic section is provided with a first capillary filled with an agarose gel and a second capillary filled with a polyacrylamide gel. An on-column detector is incorporated with the second capillary for optical detection. To fill a capillary with a gel, a solution is fed under high pressure from a first flow channel through a switching valve into a second flow channel connected to the capillary. To inject a sample in the capillary, a sample injector is connected to a switching valve passage, and a buffer solution is connected to the capillary through a flow channel and the switching valve. After switching the valve, the first passage is incorporated into the flow channel between the buffer solution and the capillary being filled. Then, the sample is electrokinetically injected into the capillary. When conducting genetic polymorphism by electrophoresis, temperature control elements are provided to maintain the capillary at a predetermined temperature and a DNA sample device is provided to heat the sample to a temperature higher than a disassociation temperature thereof for directly injecting the heated sample into the capillary.

2 Claims, 14 Drawing Sheets

OTHER PUBLICATIONS

Journal of Chromotography, 516, 1990, 33–48, Barry L. Karger et al, "Separation of DNA restriction fragments by high performance capillary electrophoresis with low and zero crosslinked polyacrylamide using continuous and pulsed electrophoresis".

Proceedings of National Academy of Science of USA, 86, 1989, pp. 2766–2770, Takao Sekiya et al, "Detection of polymorphisms of human DNA by gel electrophoresis as single-strand conformation polymorphisms".

Analytical Chemistry, 64, Jun. 1992, pp. 1221–1225, Yoshinobu Baba et al, "Preparation of Polyacrylamide Gel Filled Capillaries for Ultrahigh Resolution of Polynucleotides by Capillary Electrophoresis".

Journal of Chromotography, 559, 1991, pp. 267–283. Herbert E. Schwartz et al. "Analysis of DNA restriction fragments and polymerase chain reaction products towards detection of the AIDS (HIV.1) virus in blood".

Journal of Chromotography, 559, 1991, pp. 295–305, Barry L. Karger et al "Identification of DNA molecules by pre-column hybridization using capillary electrophoresis".

Gobinda Sarkar et al, "Screening for Mutations by RNA Single-Strand Conformation Polymorphism (RSSCP): Comparison with DNA-SSCP,", Nucleatic Acids Research, 1992, 20(4), pp. 871–878.

"Isolation of High-Molecular-Weight, Eukaryotic DNA From Cells Grown in Tissue Culture," Construction of Genomic Libraries, 1982, pp. 280–281.

METHOD FOR ANALYZING NUCLEIC ACID OR PROTEIN AND APPARATUS THEREFOR

This is a divisional application of U.S. Ser. No. 08/111,508, filed Aug. 24, 1993, now U.S. Pat. No. 5,409,586.

FIELD OF THE INVENTION

The invention relates to a method and apparatus for analyzing a nucleic acid or protein by capillary gel electrophoresis; a method for analyzing genetic polymorphism by capillary gel electrophoresis for use in gene diagnosis or gene tests required for medical purposes; a method and apparatus for producing a gel filled capillary to be used in capillary gel electrophoresis; and to a microinjector for use in injecting samples in a capillary for capillary gel electrophoresis.

BACKGROUND OF THE INVENTION

Capillary electrophoresis is superior to high performance liquid chromatography in that the amount of sample required for analysis can be less that 1/1,000 of the amount required for liquid chromatography and in that the separation performance as compared with liquid chromatography is tens of times higher. Capillary electrophoresis can be conducted in a shorter period of time than that for conventional slab gel electrophoresis and the like, because a higher voltage can be applied. Furthermore, when one end of the capillary is used as an injector, the samples can be injected automatically to provide an automated capillary electrophoresis apparatus. Capillary electrophoresis is described, for example, in Science, 222, 266–272 (1983). DNA sequencing is described in Analytical Chemistry, 62, 900–903 (1990).

Recently, capillary electrophoresis has been actively applied to many fields. In particular, nucleic acids and proteins have been analyzed as part of the recent development in biotechnological studies. In order to detect nucleic acid and proteins, ultraviolet detection and fluorescent detection have been used. For such detection, an on-column detection device that is integrated with the capillary is commonly employed.

In the analysis of nucleic acids, and particularly in DNA sequencing, the capillary electrophoresis is usually performed using a polyacrylamide gel. By this method, approximately 300 bases can be identified within about 45 minutes. Although it has been reported that DNA fragments consisting of about 10,000 bases have been separated within 20 minutes, the resolution was in the order of 1,000 bases in the case of DNA fragments consisting of thousands of bases. The analysis of DNA fragments consisting of about 10,000 bases has been described in Journal of Chromatography, 516, 33–48 (1990).

In the conventional on-column detection method with the use of a detector integrated with a capillary, the detection was performed by providing an optical path in part of the capillary. In general, an agarose gel was used as the slab gel electrophoresis for separating DNA consisting of 1,000 or more bases. In order to separate DNA having more bases than this and up to thousands of bases, it is necessary to use an agarose gel, rather than a polyacrylamide gel. However, an agarose gel has a poor light transmittance characteristic and is therefore unsuitable for on-column detection. As a result, it has been highly difficult to separate DNAs consisting of thousands of bases by capillary electrophoresis. Further, an agarose gel has heat resistance problems so it has been difficult to use such a gel in capillary gel electrophoresis where a high voltage is applied and Joule heating is created.

Genetic polymorphism, which is useful in gene diagnosis and gene tests required for medical purposes, relies on polymorphisms built up in human genes and other animals that have medical information relating to genepathy and immunological mechanisms. For example, more than 400 polymorphisms are built up in a histocompatibility antigen (HLA) gene, which closely relates to an immunological mechanism and combinations of these polymorphisms give more than 1 or 10,000 serotypes. It is particularly important in, for example, organ transplantation to determine these serotypes. Further, there is suggested a relationship between these serotypes and various diseases. Thus, the determination of HLA serotypes will become highly important in the future and a method for quickly and accurately analyzing the polymorphism is very important in the fields of diagnosis and medical examinations.

The detection of genetic polymorphism on a monobase level means the detection of a mutation in a gene arrangement and relates to the diagnosis of a number of diseases including cancer. It is suggested that gene mutation would relate to the mechanism of carcinogenesis or metastatis. Therefore, the rapid classification and determination of genetic polymorphisms and mutations of a number of specimens, if possible, will contribute greatly to the diagnosis and identification of carcinoma.

To detect genetic polymorphism on a monobase level with high sensitivity, it has been proposed, for example, by M. Orita et al in the Proceeding of National Academy of Science of U.S.A., 86, 2766–2770 (1989) to analyze the base sequence polymorphism of a DNA by using a difference in higher-order structure between single-strand DNAs (single strand conformation polymorphism, hereinafter referred to as the SSCP method). This method includes disassociating the target region on a DNA base sequence, which has been extracted by an appropriate method, into a pair of single-strand DNAs which are complementary to each other by an appropriate denaturing means and then electrophoresing these single-strand DNAs on an undenatured polyacrylamide gel. In this procedure, the migration rate of each single-strand DNA varies under the influence of the higher-order structure of the single-strand DNA and this higher-order structure is specifically determined depending on the sequence of the single-strand DNA. Thus, a sequence polymorphism differing in at least one base can be detected by taking advantage of the above-mentioned property.

Since this method of SSCP is highly convenient and enables the detection of a polymorphism due to a difference in a single base at a high sensitivity, it is thought to be quite advantageous as compared with the restriction fragment length polymorphism method and the other well known conventional method for analyzing polymorphism that uses a DNA probe specific for a sequence. In recent years, the SSCP method has been combined with the polymerase chain reaction method (PCR method) in the analysis of polymorphism or the identification of gene mutation.

It has been difficult to achieve a high separation performance and to effect quantitative analysis of electrophoretic patterns, which provide valuable information for analyzing the polymorphism, by the conventional SSCP method, wherein the electrophoresis is performed by using a slab gel. Further, additional problems exist when this method is performed, mainly the migration and detection require a long time, the denatured sample of the single-strand DNAs undergo reassociation during the procedure of packing them in a gel, and it is difficult to control the temperature during the migration which greatly affects the maintenance of the higher-order structures. Under these circumstances, one object of the present invention is to provide a method for analyzing genetic polymorphism by the SSCP method whereby the analysis can be conveniently completed within a short period of time to achieve a high separation as compared with the conventional methods. The invention further aims at enabling automatic analysis of polymorphism by the SSCP method.

Conventionally, a gel filled capillary has been produced by packing an acrylamide solution containing a polymerizing agent into a capillary by using, for example, a syringe and them effecting gelling polymerization in the capillary. However, this method suffers from a problem that air bubbles are formed in the polymerization of the acrylamide and thus the acrylamide gel thus formed is practically unusable. To counteract this problem, a method has been employed wherein the acrylamide is polymerized under a high hydraulic pressure and also wherein a carefully degassed acrylamide solution is treated by suction or vacuum and packed into the capillary. U.S. Pat. No. 4,810,456 discloses a method for polymerizing acrylamide under high hydraulic pressure. A method for vacuum injection of a degassed acrylamide solution is disclosed in Analytical Chemistry, 64, 1221–1225 (1992).

The production of a capillary gel by polymerizing acrylamide under a high hydraulic pressure has been performed by packing an acrylamide solution containing a polymerizing agent in a capillary by using, for example, a syringe and subjecting the capillary packed with the acrylamide solution to gelling polymerization under a high hydraulic pressure. This method suffers from a problem that the acrylamide solution is diluted before the polymerization of the acrylamide, and thus it is difficult to form a gel with high reproducibility of the result. In addition, the load in the capillary increases as the inner diameter of the capillary decreases, and, as a result, the injection becomes difficult. Accordingly, most of the capillaries usable in this method have an inner diameter of at least as great as 75 μm and there have been only a few reported examples of using capillaries having an inner diameter of 50 μm. Although it is possible to use, for example, a pump for packing the acrylamide solution, a long channel from the solution tank to the capillary is inevitably required when a pump is employed, and therefore, a large amount of the acrylamide solution is required. Furthermore, a considerably long period of time elapses during feeding the solution from the pump to the capillary, which causes another problem that the polymerizing agent added before the injection causes the acrylamide to gel in the flow channel.

With the other conventional method involving the vacuum or suction injection of a carefully degassed acrylamide solution and packing thereof in a capillary, there exists a problem that the vacuum injection of the acrylamide solution makes the pressure in the capillary negative, thus creating a potential for air bubbles to be formed if the degassing is insufficient.

Conventional methods of injecting a sample include gravity injection, which relies upon the difference in gravity, pressure injection, which relies upon the use of a difference in pressure and electrokinetic injection. The injection method affects the analytical accuracy and reproducibility of results with capillary electrophoresis. With these conventional methods, control is difficult since the difference in gravity or pressure is difficult to control when a minute amount of the sample is injected. In particular, a trace amount of a sample is difficult to inject by the methods of gravity injection and pressure injection. In the electrokinetic injection, on the other hand, the amount of sample to be injected is determined by the amount and duration of the applied voltage. Accordingly, a trace amount of a sample can be readily injected with high accuracy by controlling the amount and duration of the applied voltage. As a result, the electrokinetic injection method is the most commonly employed method at the present time. This method, however, suffers from a problem that the amount of a sample to be injected varies depending on the components contained therein, since the mobility varies from substance to substance.

One solution proposed for this problem has been set forth in Japanese Patent Laid-Open Application No. 253247/1988, wherein it has been proposed to meter a sample with a rotary injector and inject the sample under pressure. Specifically, the sample is sandwiched between a gel and a buffer during the step of injecting the sample. As a result, the sample is diluted with the buffer before being incorporated into the gel by pressure injection with the result that the sensitivity and separation performance are degraded due to an increase in the widening of bands caused by, for example, disorders in the band.

SUMMARY OF THE INVENTION

In order to solve the problem of performing gel electrophoresis for DNAs having thousands of bases using an agarose gel, it is an object of the present invention to perform the analysis by capillary electrophoresis using an agarose gel to achieve separation and then conducting on-column detection with a detection device packed with a polyacrylamide gel, which has an excellent light transmittance characteristic. Specifically, the steps involve: (1) connecting the agarose gel to the polyacrylamide gel by using a glass connector that is hermetically sealed with respect to the polyacrylamide gel so that the passage characteristics and the electrical conductivity are maintained for the sample that has been separated by the agarose gel; and (2) suppressing the value of the current flowing through the capillary to thereby suppress Joule heating in the capillary.

The use of an agarose gel in capillary electrophoresis serves to facilitate the separation of DNA consisting of over thousands of bases. Since a polyacrylamide gel that has excellent light transmittance is used in the detection section, the DNA separated by the agarose gel can be optically detected by an on-column detection device while maintaining the high separation performance achieved by using the agarose gel. Further, Joule heating can be suppressed by selecting an appropriate buffer concentration.

It is another object of the present invention to provide a method for analyzing genetic polymorphism by the SSCP method whereby the analysis can be conveniently completed within a short period of time and with a high separation performance by using capillary electrophoresis with an on-column detection unit employed as the electrophoresis/detection means. Further, a sample carrier is provided with a thermostatic chamber whereby an example can be heated to the disassociation temperature at the time of injection, and thus the sample can be directly injected into the gel while being maintained at the disassociation temperature. Furthermore, the capillary temperature can be controlled by a thermostatic plate during the electrophoresis.

Since capillary electrophoresis for detecting genetic polymorphism can be performed with on-column detection, the electrophoretic pattern of a sample, which is expected to show higher-order structure polymorphism, can be detected as two peaks which are fully separated from each other. Regarding the amount of a single strand DNA per band, bands which are detected in an overlapping state due to higher-order structures and those which are detected in a separated state can be read directly as numerical values based on the height of each peak. Thus, the pattern can be analyzed with high precision.

When the SSCP analysis is carried out by using capillary electrophoresis, the accuracy of temperature control of an electrophoretic carrier can be easily improved. When expressed in a volume/surface area ratio (V/S ratio) corresponding to the heat value per unit radiating surface area, the radiation efficiency achieved by electrophoresis with the use of a capillary of 100 µm in diameter (V/S=0.025 mm) is about twenty times as high as one achieved by electrophoresis with the use of a slab gel of 1 mm in thickness (V/S=0.5 mm), which is the conventional practice.

According to the mechanism of separating polymorphism by the SSCP method, polymorphisms are separated by taking advantage of a difference in stable higher-order structure between sequences under given temperature conditions. Mainly, it is necessary in the SSCP method to maintain a higher-order structure specific for the sequence depending on the temperature during the electrophoresis. Thus, it is not significant that the temperature of the electrophoretic carrier remain uniform throughout the electrophoretic operation. From this point of view, sequence polymorphisms which cannot be separated by the conventional methods can be separated and detected by using the SSCP method with capillary electrophoresis.

It is also highly advantageous to use Peltier elements in the temperature controller plate for the capillary. A Peltier element enables both cooling and heating by alternating the polarity of the voltage that is applied to the element. According to the present invention, the temperature of the capillary electrophoresis apparatus should be exactly controlled at a temperature around room temperature, and it is important to select and control the heating and cooling operations at arbitrary points of time. Thus, the temperature of the apparatus can be controlled in an overall temperature range of about 5° to 60° C. at an accuracy of ±0.1° C. Further, the time required for the electrophoresis is remarkably shortened to 1/6 to 1/10 of that required in the conventional SSCP method with the use of a slab gel, which conventionally requires 2 to 5 hours or longer.

By using capillary electrophoresis for the genetic polymorphism, even a minute amount of a sample can be sufficiently electrophoresed and detected. In the case of capillary electrophoresis with UV-absorption detection method, $5 \times 10^8$ mol/l (in terms of concentration) or $5 \times 1/10^{19}$ g (in terms of absolute amount) of a sample can be sufficiently detected. Compared with the detection sensitivity of the conventional method that uses a slab gel, these detection values indicate sufficiently high sensitivity. A higher sensitivity can be obtained, if required, by fluorescent labeling. Furthermore, any DNA sample can be electrophoresed as single-strand DNAs by heating the sample to the DNA disassociation temperature and then introducing it into the gel in a state where the DNA is disassociated into single-strand DNAs.

In the case of the conventional electrophoresis method that uses a slab gel, a port for injecting a sample into the gel employed as an electrophoretic carrier is located in a buffer tank. It is therefore significantly difficult to heat the sample to the DNA disassociation temperature or thereabove. Thus the sample is injected into the gel by way of an electrophoretic buffer at almost the same temperature as the gel. As a result, there arises some problem with the possibility of reassociation of the strands that are complementary to each other, which may occur in the step of the injection of the sample into the gel. Accordingly an appropriate denaturant should be added in the step of the injection of the sample into the gel. These problems occur because the temperature that allows a stable higher-order structure to be maintained falls within a range where reassociation is liable to occur.

In capillary electrophoresis practiced according to the present invention, however, a sample can be heated to the DNA disassociation temperature prior to injection and the above-mentioned problems are solved. This is because in capillary electrophoresis, a sample container is separated from an electrophoretic buffer and the sample is injected by contacting the tip of a capillary with the sample solution exclusively. In the injection step, it is therefore possible to preheat the sample to the DNA disassociation temperature. Thus, disorders in detected peaks due to a band of the double-strand DNA which is formed by the reassociation during the electrophoresis does not occur. Thus, both a sharp electrophoretic pattern can be obtained and also a higher-order structure polymorphism of all the injected DNAs can be detected. Therefore, polymorphisms can be fully detected even when a minute amount of a DNA sample is injected.

It is another object of the present invention to produce a gel filled capillary that is free from air bubbles and that can be reliably produced by using a gel solution that is fed by a pump, for example, into a flow channel connected to the capillary from another flow channel so as to prevent the gelation of the acrylamide solution in the flow channel due to adding the polymerizing agent before injection into the capillary.

By this method, since an acrylamide solution is packed in the capillary with the pump, the solution can be fed under a high pressure and an acrylamide gel can be packed in a capillary having an inner diameter of 50 µm and less. Further, since the gel solution is fed into the capillary feeding flow channel from another flow channel, the solution does not gel during the feeding operation.

It is a further object of the invention to provide a device for metering a sample during injection of a sample in a capillary gel electrophoresis apparatus method by using a micro-injector having a rotary channel switching valve and a conductive partition provided between a buffer tank and a sample metering section. By the present invention, a minute amount of a sample can be injected into the capillary with highly reproducible results. Furthermore, since a conductive partition portion is located between the buffer tank and the sample metering section, disorders in the sample and the diffusion of the sample problem can be suppressed, such as dilution, and therefore the widening of bands can be reduced. Since the conductive partition is used between the buffer tank and the sample metering section, a high voltage required for electrophoresis can be applied and the electrophoresis is not interfered with by the injector.

DETAILED DESCRIPTION OF THE PREFERRED EMBODIMENTS

Figure 1:
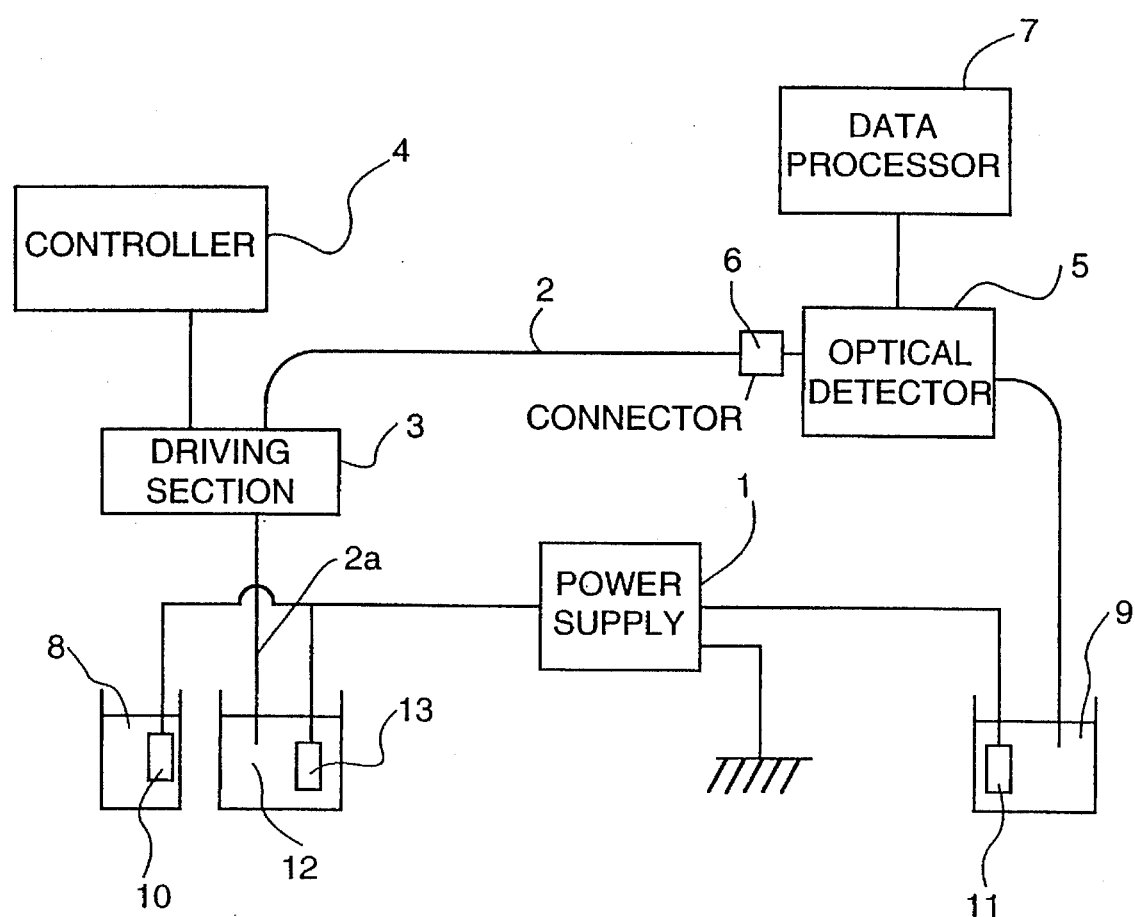
FIG. 1 is a block diagram showing the construction of a capillary electrophoresis apparatus according to an embodiment of the present invention.

FIG. 1 shows a first embodiment of the present invention in block diagram form. The capillary electrophoresis apparatus has a high voltage power source section 1, an electrophoretic section 2, a driving section 3, a controller section 4 for controlling the driving section 3, an on-column optical detection section 5, a connector 6 for connecting the electrophoretic section 2 to the optical detection section 5, shown in greater detail in FIG. 3, and a data processing section 7 for processing the data detected by the optical section 5. The high voltage power source 1 has an output voltage of between 0 to 30 kV with a polarity switching capability whereby the voltage is applied between a sample container 8 and a buffer tank 9 via electrodes 10 and 11, and between another buffer tank 12 and the buffer tank 9 with the use of electrodes 13 and 11.

The driving section 3 is actuated by a pulse motor (not shown) to control movement in the x, y and z directions of a capillary tube comprising the electrophoretic section 2. The movement of the capillary tube in the x, y and z directions can be performed by programming the distances along these axes in order to enable automated movement of the capillary tube between the electrolyte buffer tank 12 and the sample container 8. Automated use of the apparatus is important since the apparatus is intended to handle the processing of many samples, one after another for automated analysis.

To inject a sample into the capillary electrophoresis section 2, the electrokinetic injection method is used, which relies upon migration of the sample through the gel. First, the tip 2a of the capillary tube is removed from buffer tank 12 with no voltage applied between the electrodes by driving section 3 to immerse the tip in the sample container 8. Following the positioning of the capillary tube in the sample container 8, a voltage of a given polarity is applied between electrodes 10 and 11 from power source section 1. By controlling the voltage that is applied and the duration, a given amount of the sample in the sample container 8 is injected by migration into the tip of the capillary by electrophoresis. Next, the glass capillary is returned to the buffer containing tank 12 and the voltage is again applied. This causes the electromigration of the sample in the electrophoretic section 2.

As an example of the capillary gel electrophoresis apparatus of the present embodiment, the electrophoretic section 2 is a fused silica capillary of 50 μm in inner diameter, 375 μm in outer diameter and 50 centimeter in length. A 0.3% agarose gel is used in the capillary tube, with the concentration of the gel being appropriately selected in accordance with the molecular weight of the components being separated. In the optical detection section 5, a glass capillary packed with a 3% T (g % of acrylamide) and 0.5% C (g % of NN-methylenebisacrylamide in acrylamide) polyacrylamide gel is used. The polyacrylamide gel is prepared by using N,N,N',N'-tetramethylethylenediamine as a polymerizing agent and ammonium peroxydisulfate. When a DNA consisting of over thousands of bases is to be separated, it is preferable to use a polyacrylamide gel of 5% T or less.

The optical detection section 5 preferably includes a UV absorption detector for high performance liquid chromatography modified for on-column detection. The detector can preferably measure absorbance at 260 nm, which corresponds to the DNA measurement wavelength. The data thus obtained in the optical detection section 5 is successively transmitted to the data processing section 7, wherein the data is recorded and processed.

Figure 2:
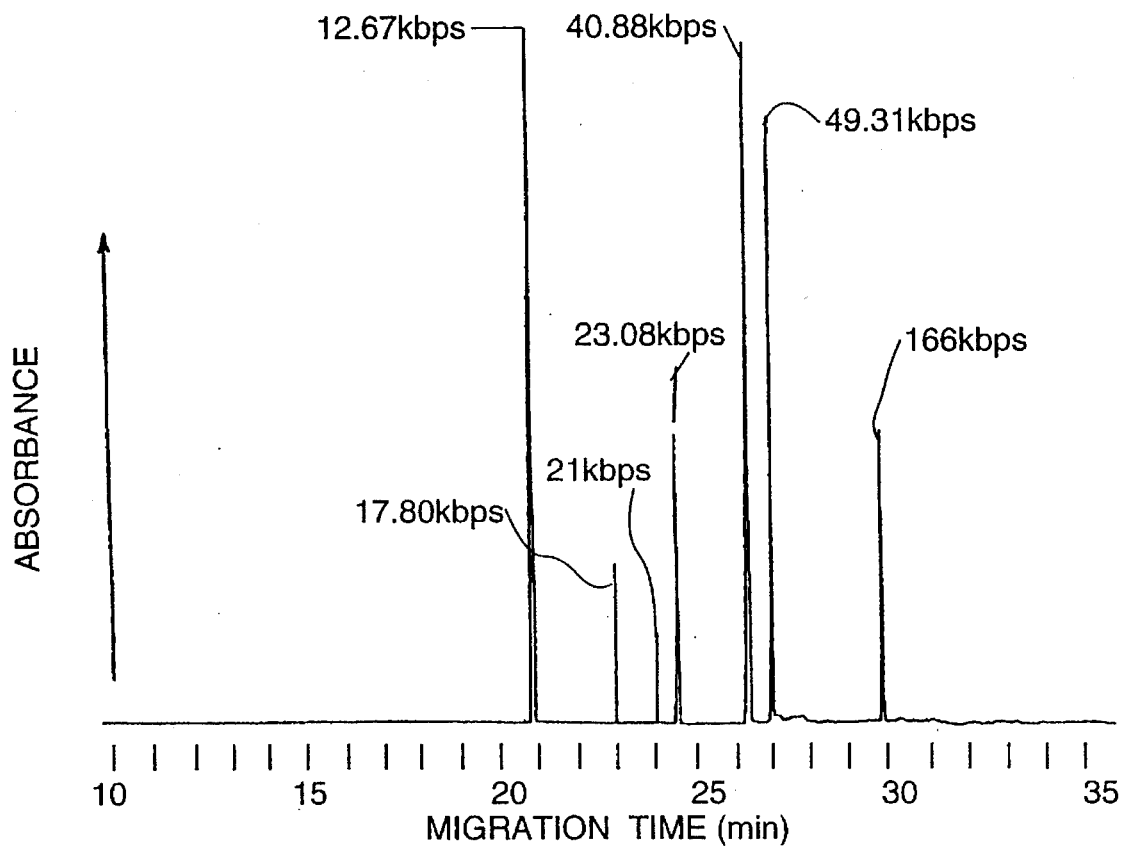
FIG. 2 is a diagram showing the results of analysis of a DNA fragment obtained by using a capillary electrophoresis apparatus according to an embodiment of the present invention.

FIG. 2 shows one example of a result obtained by the analysis of a DNA fragment with the capillary electrophoresis apparatus arrangement shown in FIG. 1 when used according to the conditions set forth in the following Table 1. The DNA fragment used in this example is a mixture prepared by completely digesting a mixture of T4dC*-DNA with T4dC-DNA, which are marketed as a DNA molecular weight marker, with a restriction enzyme Bgl I. As FIG. 2 shows, this mixture can be completely separated within 30 minutes.

TABLE 1

| Item | Condition |
| --- | --- |
| capillary | i.d.: 50 μm, o.d.: 375 μm, length: 50 cm |
| agarose gel | 0.3% agarose H |
| acrylamide gel | 3% T, 0.5% C |
| buffer | 90 mM Tris-borate, pH 8.3 2.5 mM EDTA |
| applied voltage | 7.5 kV |
| sample | T4dC/T4dC DNA mixture digested with Bgl I |
| injection method | electrokinetic injection 7.5 kV, 1 s |

Figure 3:
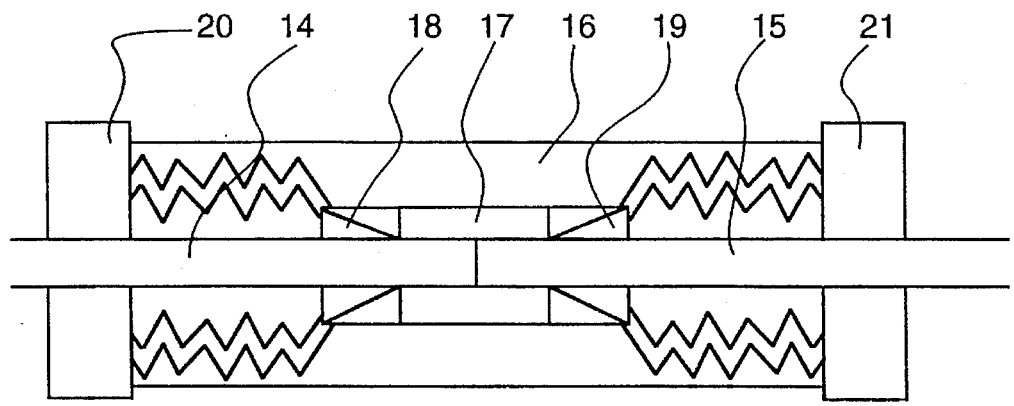
FIG. 3 is a diagram of a connector used to connect the optical detection section with the capillary tube.

One embodiment of the device used for making the connection of the glass capillary packed with an agarose gel to the optical detection section, which is packed with the polyacrylamide gel is set forth in detail, schematically, in FIG. 3. A glass capillary 14 is packed with an agarose gel, for example according to the conditions set forth in Table 1 above, for the electrophoretic section and another glass capillary 15 packed with a polyacrylamide gel is prepared for the optical detection section. These sections are prepared separately and then after each are packed with their respective gel, are inserted into a glass capillary connector 17 fixed in a fitting 16. The glass capillaries are fixed by aligning them in the same straight line and applying a force thereto by using tube gripping pressers 18 and 19 and set screws 20 and 21. The pressers have a bellows-like device that exerts pressure on the capillaries toward their connection point to maintain the capillaries in contact with each other. Preferably, the glass capillary connector 17 is also packed with a polyacrylamide gel so that the capillaries are inserted therein and fixed in such a manner as to push out the gel as the connection is established to ensure a good connection therebetween.

Figure 4:
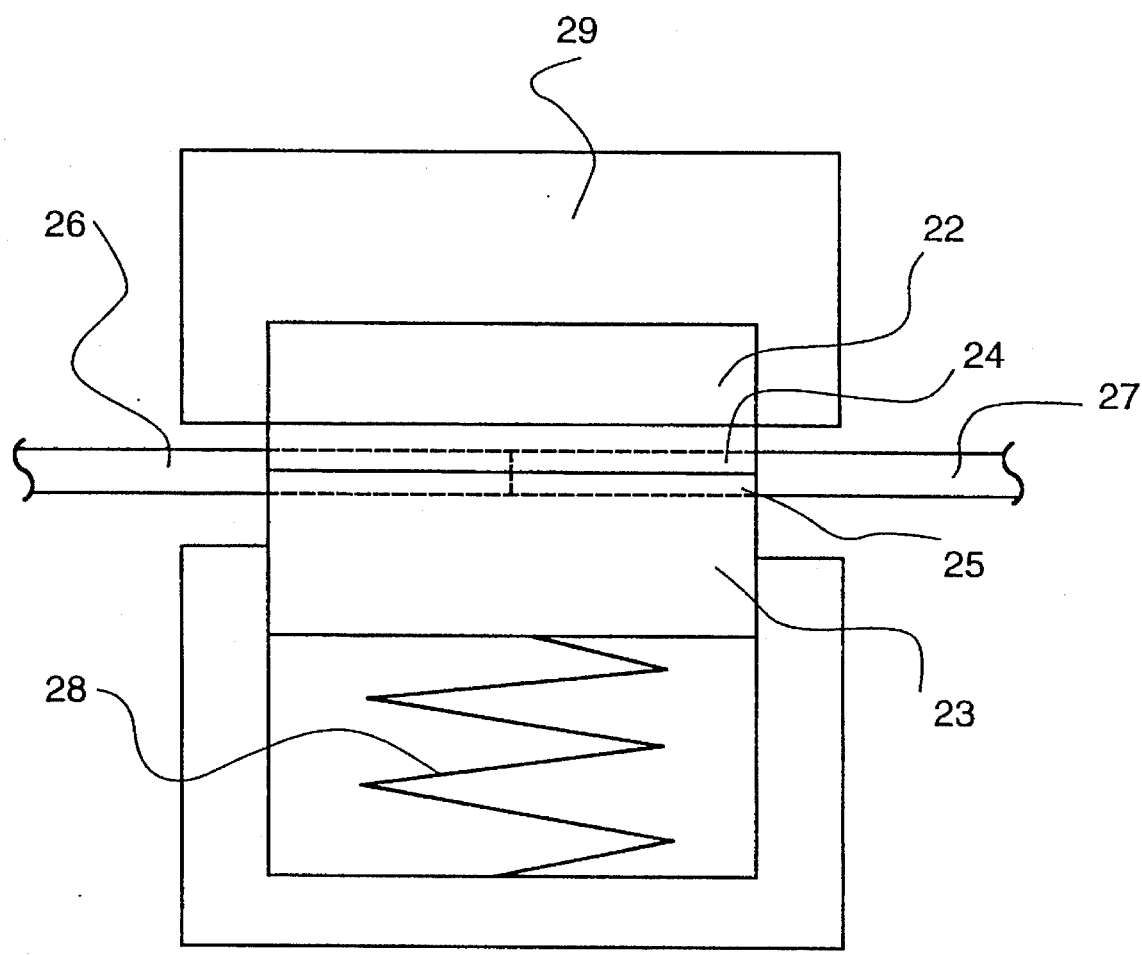
FIG. 4 is a diagram of the construction of a connection of the optical detection section to the capillary tube.

FIG. 4 shows another example or embodiment of a connector that can be used for joining the agarose gel packed capillary tube to the polyacrylamide gel packed tube in the optical detection section. Grooves 24 and 25 for the respective glass capillaries are formed on quartz glass plates 22 and 23. The grooves can be formed by a conventional manner, such as by machining or chemical etching. A glass capillary 26 for the electrophoretic section 2 is packed with an agarose gel and another glass capillary 27 for the optical detection section 5 is packed with a polyacrylamide gel separately from one another. Then the glass capillaries 26 and 27 are put in groove 25 of the quartz glass plate 23 and the quartz glass plate 22 is pressed into contact therewith by a spring 28 contained within an outer box 29. The two quartz plates are closely pressed together, and are preferably provided with a polytetrafluourethylene seal to thereby prevent any leak between the glass capillaries. Alternatively, the quartz glass plate may be replaced by polytetrafluourethylene plates. Further, preferably a polyacrylamide gel is previously applied between the plates so that the gel is squeezed out of the joint as the plates are pressed together.

Figure 5:
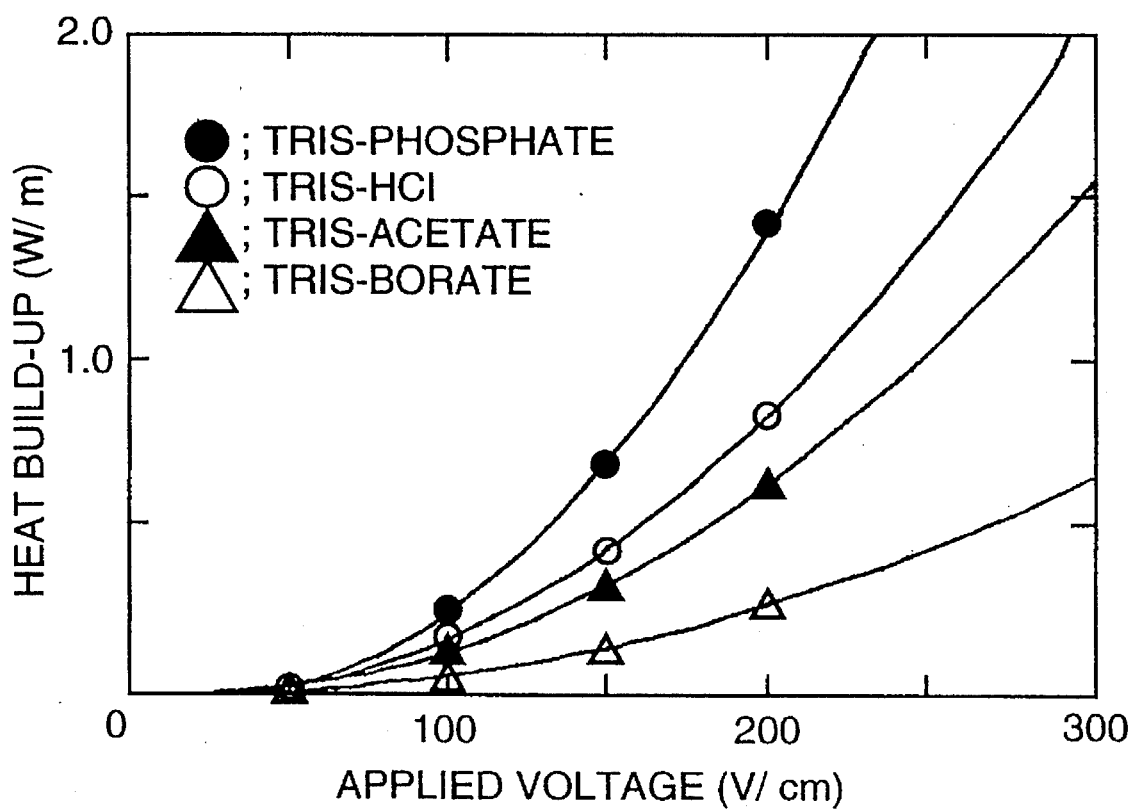
FIG. 5 is a graph of an experiment showing the relationship between applied voltage and heat for various buffers.
Figure 6:
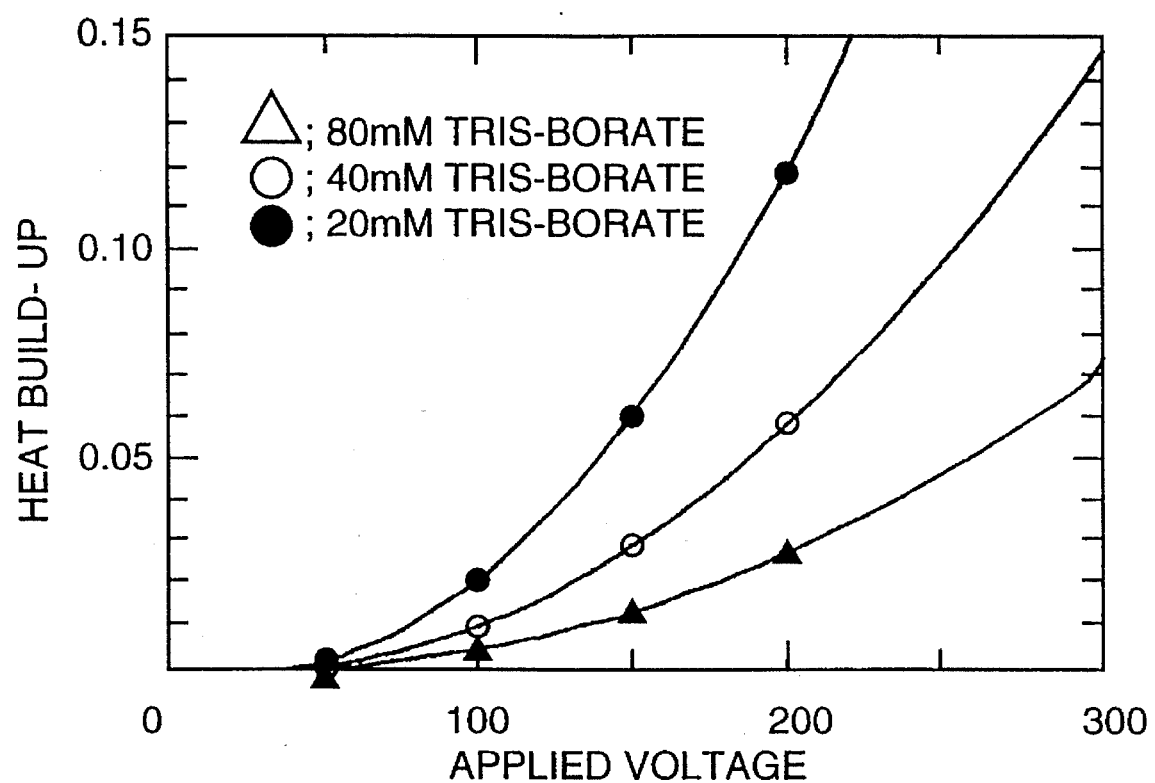
FIG. 6 is a graph of an experiment showing the relationship between applied voltage and heat for various buffers.

FIGS. 5 and 6 disclose the relationship between heat buildup and the buffer that is used in the capillary electrophoresis apparatus. In general, a current flowing through a solution depends on ions contained in the solution. The intensity of the current flowing in the capillary is affected by the buffer used therein. The relationship between the applied voltage and the heat buildup for various buffers is shown in FIG. 5. The relationships between applied voltage and heat buildup at various concentrations of a borate buffer are examined and shown in FIG. 6.

To develop the results shown in FIG. 5, various buffers were used. Each buffer had a concentration of 80 mN and a pH value of 8.3. The capillary used in obtaining the results was a glass capillary of 75 μm in inner diameter and 50 cm in length, packed with a 0.3% agarose gel.

The result of the experiment shows, in FIG. 5, that the heat buildup decreases in the order of Tris-phosphate, Tris-HCl, Tris-acetate and Tris-borate and the heat buildup caused by using the Tris-borate buffer, which shows the least buildup, corresponds to about ⅕ of that caused by using the Tris-phosphate buffer. Further, the heat buildup caused by using a glass capillary at 50 μm in inner diameter and 50 cm in length corresponds to about ⅓ of that caused by using a glass capillary of 75 μm in inner diameter and 50 cm in length. A series of the test results given in FIG. 2 and FIG. 5 suggest that the measurement can be effected when the heat buildup is 0.06 W/m or below.

Based on these results, it is considered that a Tris-borate buffer is advantageous as a buffer for suppressing the value of the current flowing in a capillary. Thus, the relationships between the applied voltage and the heat buildup at various concentrations of a borate buffer were examined, and FIG. 6 shows the results. These results were obtained by using a glass capillary of 50 μm in inner diameter and 50 cm in length packed with a 0.3% agarose gel.

The results shown in FIG. 6 reveal that the heat buildup is proportional to the buffer concentration and is reduced by half when the buffer concentration is halved. It is thus shown that the heat buildup in a capillary can be suppressed at a level of 0.06 W/m or below by maintaining the concentration of the Tris-borate at 80 mN or less, when a common level (about 150 V/cm) of a voltage is applied. It should be noted that a lower concentration of the buffer does not always give a better result, since the buffer also contributes to the maintenance of the appropriate pH value.

According to experiments carried out in accordance with the present invention, the concentration of the buffer should be at least 10 mN. When the impressed voltage is 200 V/cm or above, the use of a Tris-borate buffer of a concentration of 40 mM has also been found to be no problem. When a glass capillary of 50 μm or less in inner diameter is used, the ration of the outer surface area, where the heat is radiated, to the inner volume of the glass capillary, where Joule heating occurs, increases and thus the heat radiation efficiency is improved.

The second embodiment of the present invention is directed to detecting a genetic polymorphism on a monobase level, for example. As a target site to be detected, a region consisting of 171 bp is selected from a human factor IX gene. It is known that this gene site contains 12 types of polymorphisms due to point mutation, and the following embodiments of a capillary electrophoresis apparatus is directed to detecting a mutated sequence on a monobase level. See Gobinda Sarkar et al, Nucleatic Acids Research, 20 (4), 871–878.

The human DNA analyzed for purposes of describing this embodiment of the invention is extracted from specimen cells in accordance with the method of Maniatis (see Cloning, pp. 280–281 (1982)), wherein 1 μg of the above-mentioned genome DNA is dissolved in 100 μl of a solution of 50 mM KCl, 10 mM Tris-HCl (pH 8.3) and 1.5 mM MgCl$_2$ together with 200-μM portions of dATP, dCTP, dGTP and dTTP oligonucleotide primer prepared at a molar ratio of 20 pmol:20 pmol. Then 2.5 units of a polymerase derived from *Thermus aquaticus* (Taq-Polymerase) is added thereto. After capping with 40 μl of a mineral oil, a heating cycle of 92° C. for 2 minutes, 55° C. for 2 minutes and 72° C. for 2 minutes is repeated 40 times to thereby specifically amplify the double-strand DNA at the target site. Then the mineral oil is removed from the reaction mixture and 250 µl of 5M $CH_3COONH_4$ in ethanol is added. The mixture is centrifuged at 0° C. at 14000×g for 30 minutes and the solution of the upper part is removed (ethanol precipitation). The precipitate from ethanol (in the form of pellets) is washed with 80% ethanol (ethanol rinse: desalting) and dried. Then the precipitate is dissolved in 50 µl of a solution of 10 mM Tris-HCl (pH 7.9), 1.0 mM EDTA and 20 mM $CaCl_2$ and the resulting solution is subjected to capillary electrophoresis.

Figure 7:
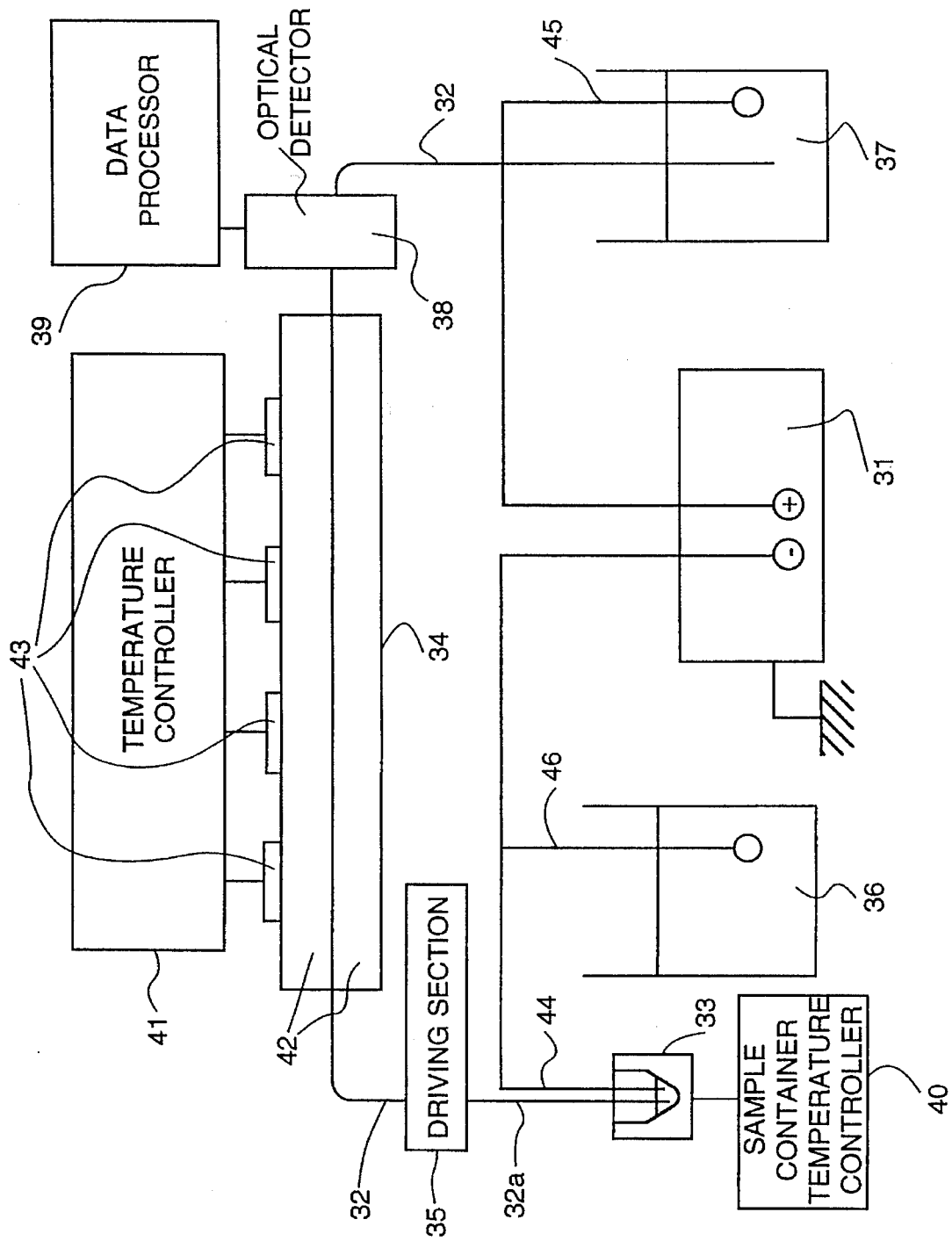
FIG. 7 is a block diagram of a capillary electrophoresis apparatus according to a second embodiment of the present invention.

FIG. 7 is a block diagram showing a capillary electrophoresis apparatus used for performing the capillary electrophoresis on the DNA according to the foregoing example. The apparatus has a high voltage power source 31, a capillary 32, a sample container and sample temperature control plate 33, a capillary holding and capillary temperature control plate 34, a driving section 35, buffer tanks 36 and 37, on-column optical detection section 38, and a data processing section 39 for processing the data detected in the optical detection section 38. The sample temperature control plate 33 and the capillary temperature control plate 34 are connected respectively to temperature controllers 40 and 41, which are independent from each other. In particular, the capillary temperature control plate 41 is arranged so that the temperature can be controlled over a range of 5° to 60° C. within an accuracy of ±0.1° C. along the capillary axis.

In the capillary temperature control plate according to this embodiment, the temperature of an aluminum plate 42 is controlled with Peltier elements 43 for both cooling and heating by altering the polarity of the voltage applied to the Peltier elements. The sample temperature controllers 33 and 40 are constructed to heat the sample of the DNA to its disassociation temperature. The use of the Peltier elements also enables a construction whereby a sample can be injected at water freezing temperature, though it is not discussed in this example.

With the high voltage power source section 31, a voltage of 0 to 30 kV can be output and the polarity of the output voltage can be readily switched over. The voltage is applied between the sample container 33 and the buffer tank 37 by using electrodes 44 and 45; and between the buffer tank 36 and the other buffer tank 37 by using electrodes 46 and 45.

To inject a sample into the capillary gel electrophoretic apparatus, the sample is first heated to a given temperature. The tip of the glass capillary 32a is immersed in sample container 33. Then the sample in the container is injected by electrophoresis into the glass capillary 32 by applying a voltage with a given polarity between electrodes 44 and 45. The amount of the sample injected is controlled by the duration and amount of applied voltage. Thereafter, the tip of the glass capillary 32a is moved into the buffer tank 36 and electrophoresis proceeds by applying a given voltage between electrodes 46 and 45.

In one example of using the capillary electrophoretic apparatus of FIG. 7 is given by the table of conditions set forth in the following Table 2, with the results shown in FIGS. 8 to 10.

TABLE 2

| Item | Condition |
| --- | --- |
| capillary | i.d.: 75 µm, o.d.: 375 µm, length: 50 cm |

TABLE 2-continued

| Item | Condition |
| --- | --- |
| | (effective length: 35 cm) |
| polyacrylamide gel | 3% T, 0.5% C |
| buffer | 90 mM Tris-borate, pH 8.3 |
| | 2.5 mM EDTA |
| applied voltage | 10 kV |
| injection method | 5.0 kV, 5 s |
| sample temp. at injection | 85° C. |
| capillary temp. | 40° C. |

The conditions in Table 2 are given merely by way of example, and other conditions regarding gel composition, buffer composition, applied voltage and preset temperature can be used to achieve the advantages of the invention as set forth herein.

Figure 8:
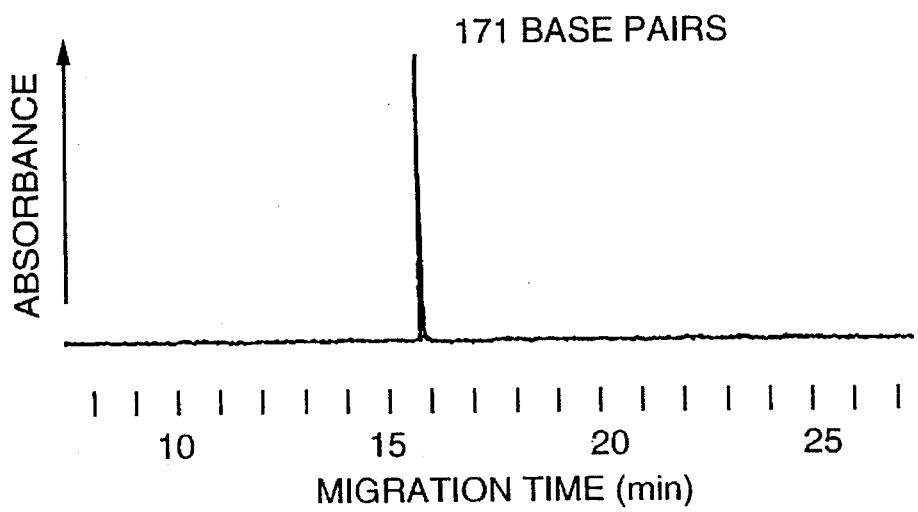
FIG. 8 is a diagram showing the electrophoretic pattern.

FIG. 8 shows the results of the electrophoresis wherein a target region of a sample having a mutation is amplified by the PCR method and then directly electrophoresed without affecting any operation of disassociation of the DNA into single-strand DNAs.

Figure 9:
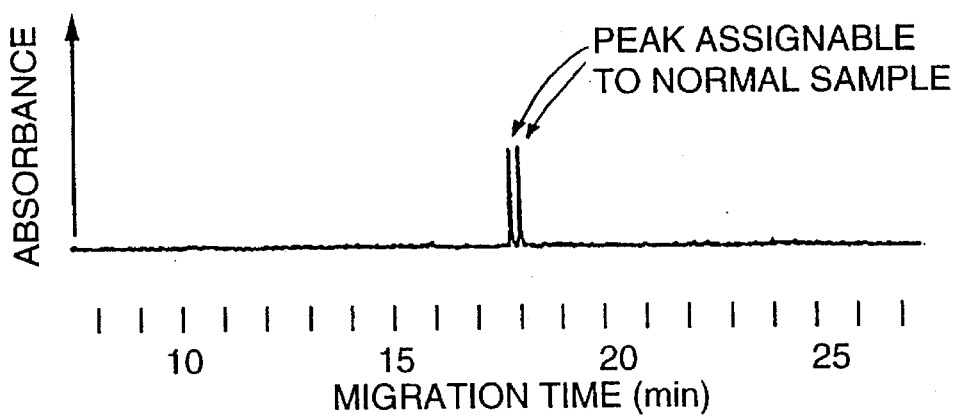
FIG. 9 is a diagram showing the result of a SSCP method analysis according to an embodiment of the present invention.
Figure 10:
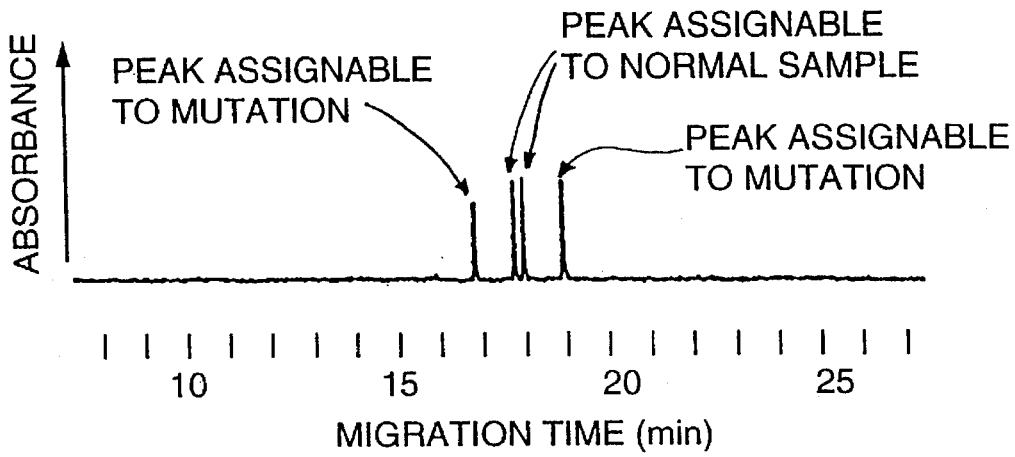
FIG. 10 is a diagram showing the result of a SSCP method analysis according to an embodiment of the present invention.

FIG. 9 and FIG. 10 each show the results of the electrophoresis wherein a target region is amplified, disassociated into single-strand DNAs and then subjected to electrophoresis. In each figure, the ordinate represents the absorbance (abs) while the abscissa represents the migration time (min) after the injection. FIGS. 8 and 9 show the results of the electrophoresis of normal samples, while FIG. 10 shows the results of electrophoresis of a heterozygote sample of a normal DNA with a mutated DNA.

In FIG. 8, a single peak is detected at a position corresponding to 16 min. A comparison with the electrophoretic patterns of other molecular weight markers suggests that this peak is assignable to a double-strand DNA of 171 dp. In contrast, four peaks are detected between 16 and 19 minutes in FIG. 10, wherein the electrophoretic pattern of a sample which has been disassociated into single-strand DNAs is shown. From among these peaks, two peaks correspond to those of normal DNAs which are detected in FIG. 9 while two other peaks are assignable to the mutated DNA.

As discussed above, the present invention makes it possible to easily and precisely detect the presence of mutations of at least one base on a gene within a short period of time. Furthermore, the use of the capillary electrophoretic apparatus of FIG. 7 makes it possible to simultaneously perform SSCP analysis at various temperatures, although operation at only one temperature is shown as an example. Since the separation of polymorphisms by the SSCP method is liable to be affected by temperature conditions, it is sometimes observed that a considerably long time is required to determine the optimum temperature conditions for separating novel polymorphisms. It is difficult to effect electrophoresis on slab gels simultaneously at various temperatures, because an apparatus of a larger scale is required. By using a capillary electrophoretic apparatus, however, in accordance with the present invention, optimum conditions can be determined in a short period of time by simultaneously performing electrophoresis under various conditions.

As a result of using the electrophoresis apparatus of FIG. 7, as taught by way of example with respect to the conditions set forth in Table 2, genetic polymorphisms due to a difference in the sequence of at least a monobase level can be precisely and conveniently detected within a short period of time as compared with the conventional SSCP method that uses a slab gel. Further, it is expected that the SSCP method, which is useful for high throughput and diagnosing gene mutation or analyzing polymorphism, but is otherwise manually intensive to operate and not readily automated, can be automated when used in accordance with the techniques of the present invention.

Thus the second embodiment of the invention contributes to the development in the fields of, for example, gene diagnosis for cancer, etc. and clinical examinations of genetic polymorphism in organ transplantation, etc.

Figure 11:
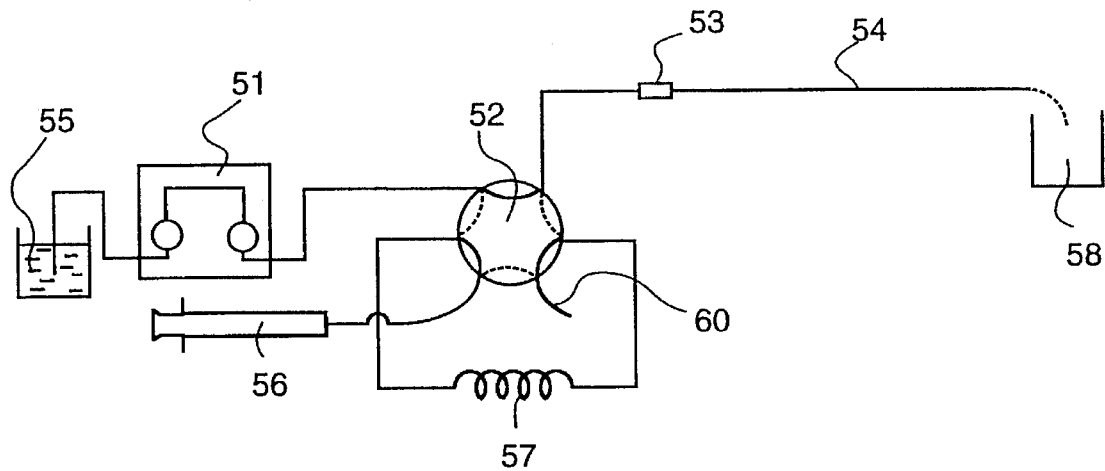
FIG. 11 is a block diagram showing the construction of an apparatus for producing a gel for a capillary gel electrophoresis used in the present invention.

FIG. 11 is directed to another embodiment of the invention relating to the preparation of a gel filled capillary by using, for example, a pump for feeding a gel solution into a first flow channel connected to a capillary from another flow channel so as to prevent the gelling of the acrylamide solution in the flow channel by the polymerizing agent before its injection into the capillary. Since an acrylamide solution is packed in a capillary by using, for example, a pump, the solution can be fed under high pressure and an acrylamide gel can be packed in a capillary of an inner diameter of 50 μm and less. Further, since a gel solution is fed into a flow channel for feeding an acrylamide solution from another flow channel, the acrylamide does not gel during the feeding operation.

An embodiment of a device for producing a gel capillary is shown in FIG. 11, wherein a solution feed pump 51, is connected to a flow channel switching valve 52 at one end and to a solution tank 55 at its other end. The solution feed pump 51 has a flow rate ranging from 0.001 to 10 ml/min and is capable of sustaining a pressure of 400 kg/cm$^2$. The solution feed pump is connected to the capillary through a switching valve 52, which may be a 6-way valve. For connecting the capillary, a capillary connector 53, such as a set screw is used.

Figure 12A:
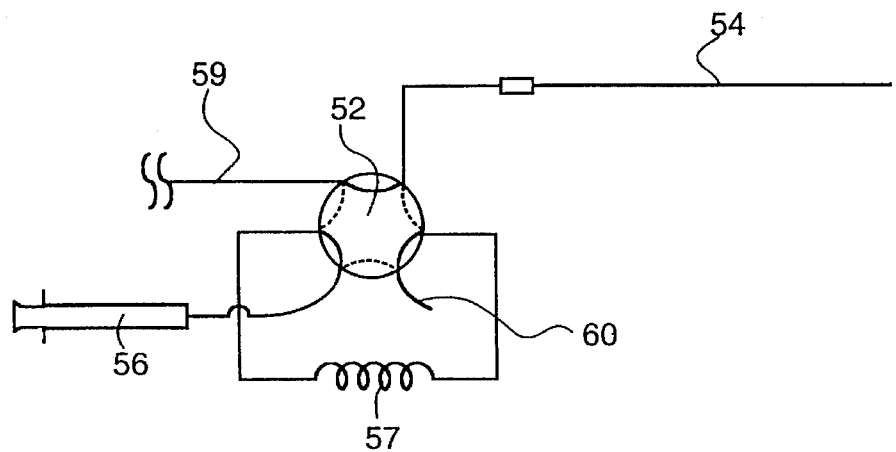
FIG. 12(a) and 12(b) show a schematic sectional view of a flow channel connection and switching device used in an embodiment of the present invention.

An acrylamide solution is injected into a capillary 54 in the following manner. First, the solution is fed from a solution tank 55 to a waste solution tank 58, which is disposed at the far end of the capillary 54. As shown in FIG. 12(a), the solution flows from solution feed pump 51 through flow channel 59 through switching valve 52 toward the capillary 54 through a channel in the switching valve represented by a solid line. Next an acrylamide solution, to which a polymerizing agent is added by using a syringe 56, is injected into a loop 57 provided in switching valve 52. The excess acrylamide solution is discarded through a drain 60.

Figure 12B:
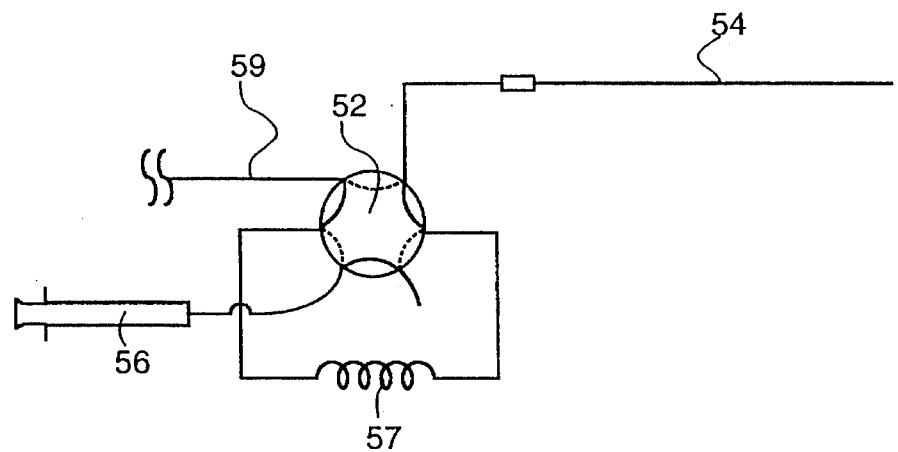

Once the switching valve 52 is switched over, the flow channel as represented by the solid line in FIG. 12(b) provides a solution fed from the solution pump 51 to pass through the flow channel 59 and push out the acrylamide solution in loop 57 until it reaches the capillary 54. This packs the acrylamide solution into the capillary. In order to prevent the acrylamide solution from being diluted by contact with the solution contained in the solution tank 55, the acrylamide solution, to which the agent has been added by using syringe 56, is injected into the loop 57 and then a small amount of air is blown into the loop 57 to form an air gap between the solution contained in tank 55 and the acrylamide solution.

In one example of producing a capillary gel, a fused silica capillary of 50 μm in inner diameter, 375 μm in outer diameter and 50 cm in length is used as the capillary 54. The composition of the acrylamide solution is 3% T (g % of acrylamide) and 0.5% C (g % of N,N'-methylenebisacrylamide in acrylamide). The acrylamide gel is prepared by using N,N,N',N'-tetramethylethylenediamine as a polymerizing agent and ammonium peroxydisulfate. When a DNA fragment is measured by using a capillary gel produced in this example, the absorbance at 260 nm corresponding to the measurement wavelength of DNA is determined by using an UV absorption detector for HPLC modified for on-column detection.

Figure 13:
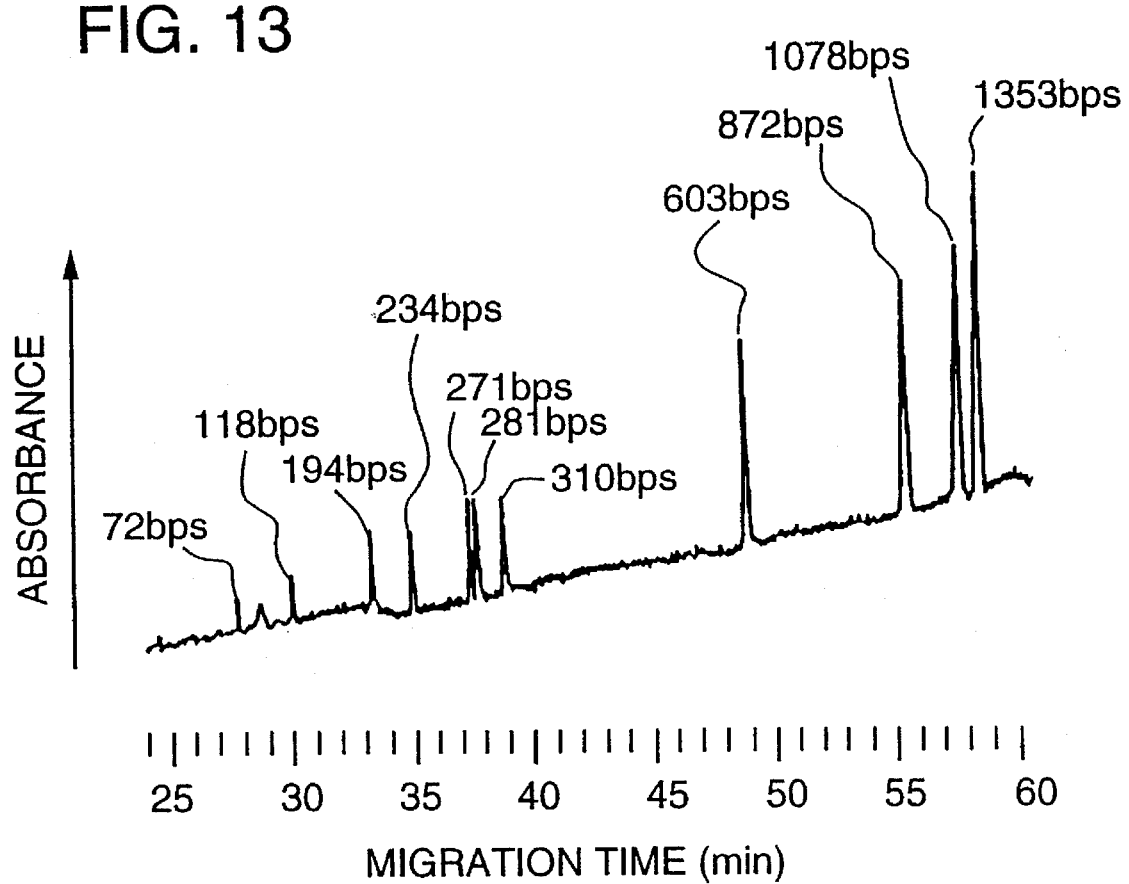
FIG. 13 is a diagram showing the results of analysis of a DNA fragment obtained according to an embodiment of the method of the present invention.

FIG. 13 shows the results of an example of the analysis of a DNA fragment obtained in an example of the embodiment of producing a capillary gel of the present invention, while Table 3 shows the measurement conditions therefor. As a result, it is proved that a mixture which is obtained by completely digesting φx 174 DNA with a restriction enzyme Hae III can be completely separated within 60 minutes.

TABLE 3

| Item | Condition |
| --- | --- |
| capillary | i.d.: 50 μm, o.d.: 375 μm, length: 50 cm |
| acrylamide gel | 3% T, 0.5% C |
| buffer | 90 mM Tris-borate, pH 8.3 2.5 mM EDTA |
| applied voltage | 5.0 kV |
| sample | φX 174 DNA/Hae III digestion product |
| injection method | electrokinetic injection 5.0 kV, 5 s |

According to this embodiment of the present invention for producing a gel filled capillary for use in capillary gel electrophoresis, the formation of air bubbles in the polymerization step is suppressed by switching over the channel used as a flow channel for feeding a solution into a capillary to thereby feed a gel solution from another channel to pack in the gel in the capillary, and then polymerizing the acrylamide. Further the acrylamide solution can be fed under a high pressure since the solution is packed in the capillary by using a pump, for example. Thus, even a capillary having an inner diameter of 50 μm or less can be packed with an acrylamide gel. Furthermore, the acrylamide gel does not gel during the feeding operation since a gel solution is fed from another flow channel.

FIGS. 14(a) and 14(b), 15(a) and 15(b) and 18 show an embodiment of the invention directed to providing a rotary channel switching valve used for feeding a sample into a capillary and, further, to providing a conductive partition that is provided between a buffer tank and a sample metering section. By this embodiment of the present invention, a minute amount of a sample can be injected into the capillary with a high degree of accuracy. Furthermore, since a conductive partition is located between the buffer tank and the sample metering section, disorders in the sample and the problem with diffusion of the sample by dilution can be suppressed and therefore the widening of the bands can be reduced. Since the conductive partition is used between the buffer tank and the sample metering section, the high voltage required for electrophoresis can be applied with no interference of the electrophoresis.

Figure 14:
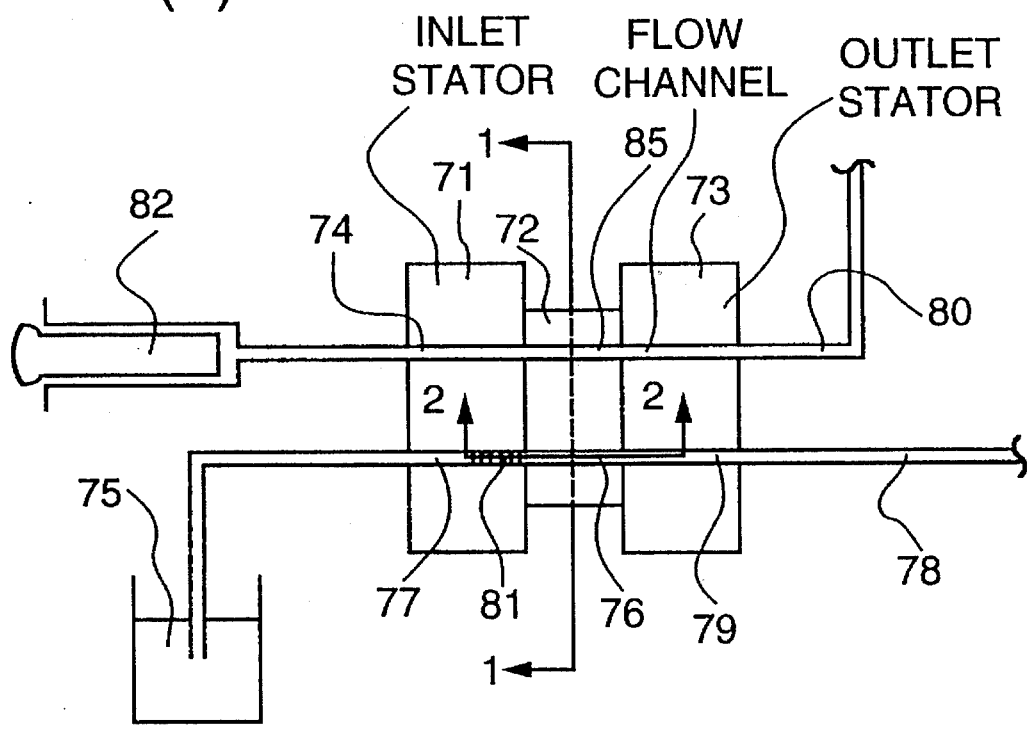
FIG. 14(a) is a schematic sectional view of part of a capillary gel electrophoresis apparatus having a micro injector constructed according to an embodiment of the present invention.
FIG. 14(b) is a partial sectional view of the rotor of the micro injector of FIG. 14(a) taken along line 1—1.
Figure 14:
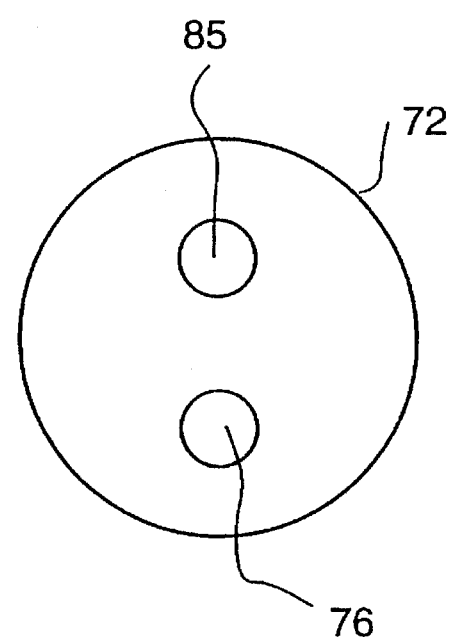

FIG. 14(a) is a schematic sectional view of part of an apparatus for a capillary gel electrophoresis apparatus having a construction of a microinjector embodying the present invention. In FIG. 14(b), a partial sectional view of the microinjector taken along line 1—1 is shown.

The microinjector, according to a preferred embodiment of the present invention as shown in the figures, has an inlet stator 71, a rotor 72 and an outlet stator 73. The inlet stator 71 is provided with a sample needle port 74 and a flow channel 77 for connecting a buffer tank 75 to a sample metering section 76 in the rotor 72. A conductive partition 81 is located in the flow channel 77 so as to prevent the sample from being diffused into the buffer tank 75. Examples of usable conductive partitions include porous glass, a film of a polymer such as cellulose, or a gel such as an acrylamide gel. The outlet stator 73 is provided with a connection port 79 for connecting the buffer tank 75 to a capillary 78 via the sample metering section 76 in the rotor 72 and a flow channel 80 with a drain. The rotor 72 is provided with a sample metering section 76 and a flow channel 85 for connecting the inlet stator 71 to the outlet stator 73. As shown in the side view of the rotor 72, in FIG. 14(b), the sample metering section 76 and the flow channel 85 are located symmetrically about the center point of the rotor 72, each having through bores of the same diameter.

Figure 15:
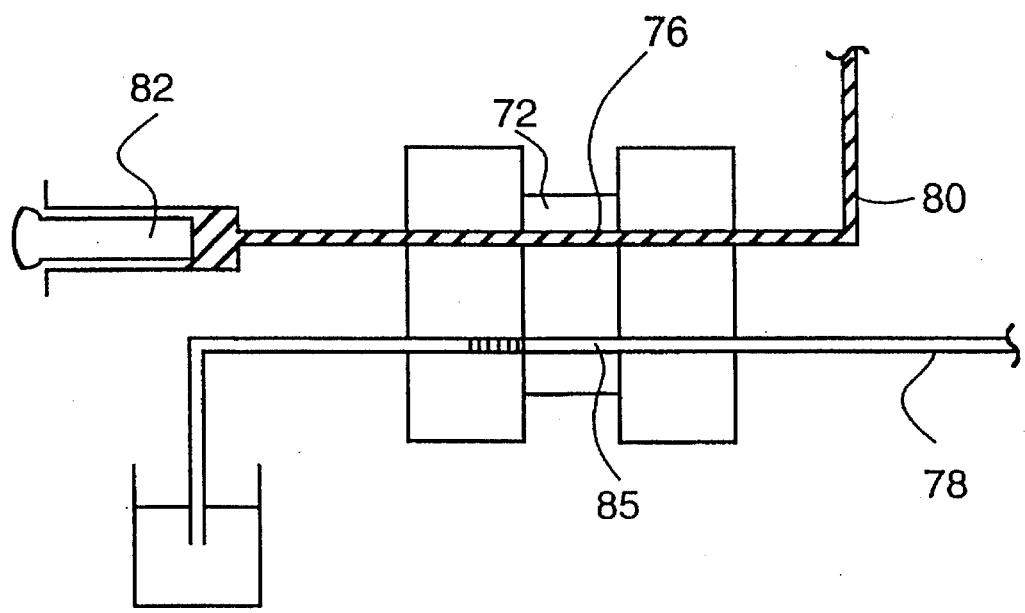
FIGS. 15(a) and 15(b) are schematic sectional views of the construction of a flow channel connector for the micro injector of the present invention.
Figure 15:
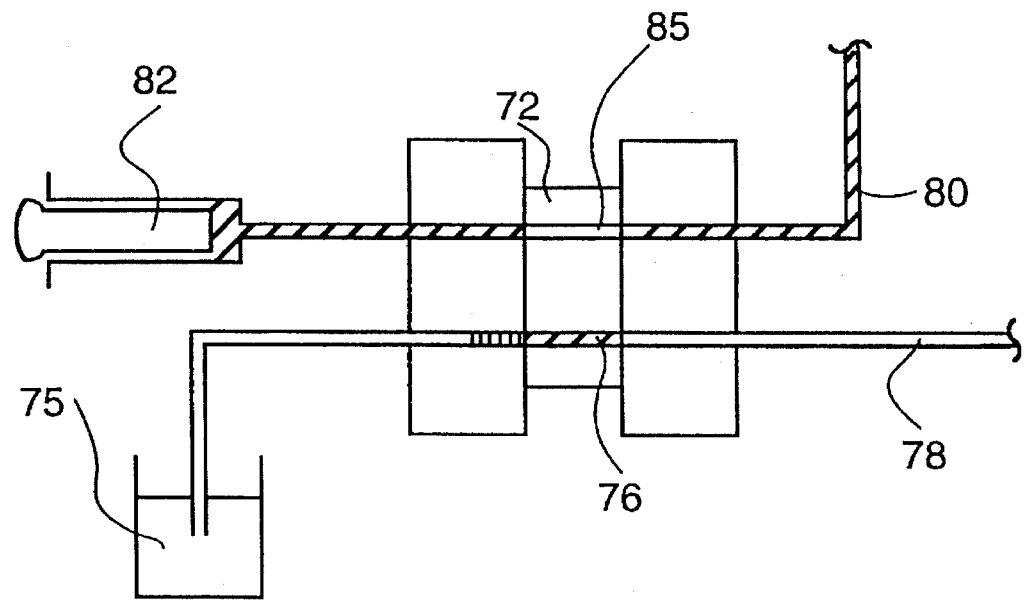

The sample is injected into the capillary through rotor 72 in the following manner. First, the sample is injected into the sample metering section 76 by using a sample injection needle 82, as shown in FIG. 15(a). An excess amount of the sample is discarded through flow channel 80. During the injection of the sample, since a buffer solution can preliminarily flow in the electrophoresis apparatus, the sample used in the previous electrophoretic operation can be removed through the capillary 78. Subsequently, the rotor 72 is rotated by 180°, as shown in FIG. 15(b) to thereby connect the sample metering section 76 filled with the sample to the flow channel located between the capillary 78 and the buffer tank 75. Finally, a voltage is applied to cause electrophoresis so that the sample migrates into the capillary 78, where it can be analyzed.

As one example of using the microinjector of the foregoing embodiment, a fused silica capillary of 50 μm in inner diameter, 375 μm in outer diameter and 50 cm in length is used as the capillary. The composition of the acrylamide solution is 3% T (g % of acrylamide) and 0.5% C (g % of N,N'-methylenebisacrylamide in acrylamide). The acrylamide gel is prepared by using N,N,N,N-tetramethylethylenediamine as a polymerizing agent and ammonium peroxydisulfate.

Figure 16:
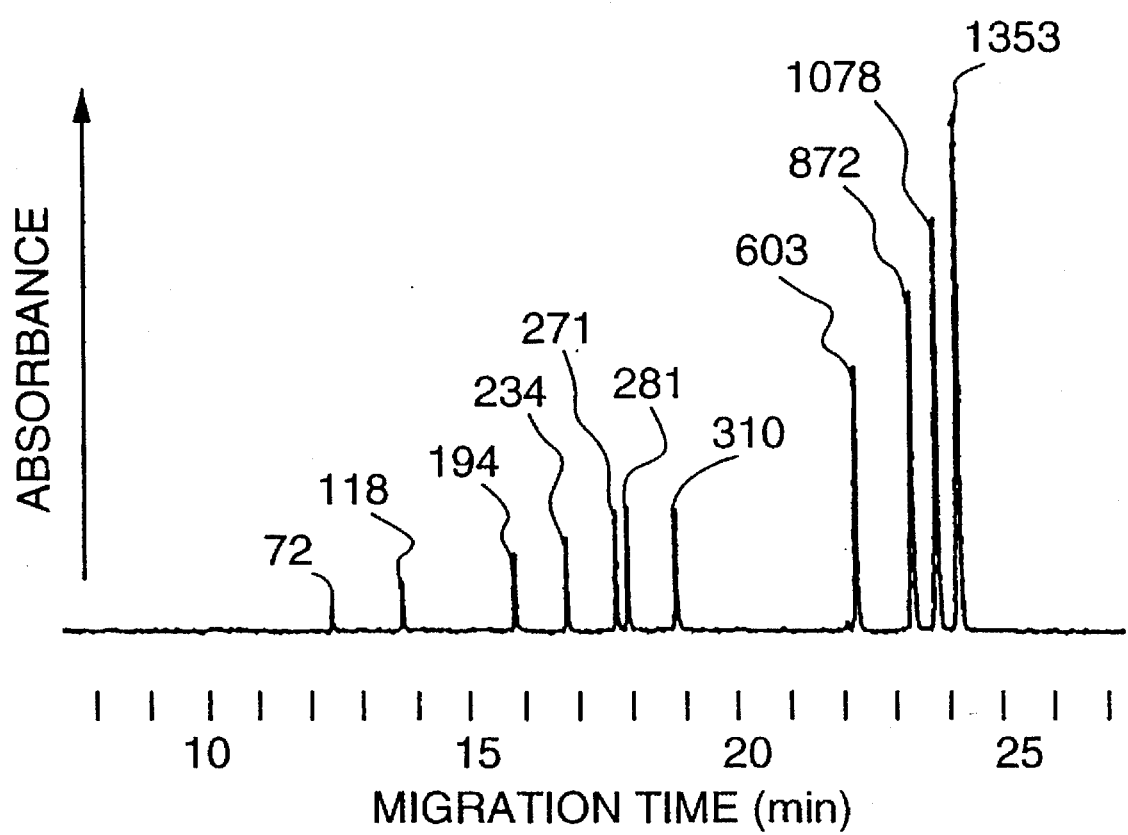
FIG. 16 is a diagram showing the results of the analysis of a DNA fragment according to an embodiment of the present invention.

FIG. 16 shows an example of the result of the analysis of a DNA fragment obtained by analyzing the DNA fragment with a capillary gel electrophoretic apparatus with the use of the microinjector according to the present invention and measuring the absorbance at 260 nm, which corresponds to the measurement wavelength for DNA, by using an UV absorption detector for HPLC modified for on-column detection. The measurement conditions are given in Table 4. The experiment showed that a mixture obtained by completely digesting φx 174 DNA with a restriction enzyme Hae III can be completely separated within 25 minutes.

TABLE 4

| Item | Condition |
| --- | --- |
| capillary | i.d.: 50 μm, o.d.: 375 μm, length: 50 cm |
| acrylamide gel | 3% T, 0.5% C |
| buffer | 90 mM Tris-borate, pH 8.3 |

TABLE 4-continued

| Item | Condition |
| --- | --- |
| | 1 mM ethidium bromide |
| | 2.5 mM EDTA |
| applied voltage | 15.0 kV |
| sample | φX 174 DNA/Hae III digestion product |

Figure 17:
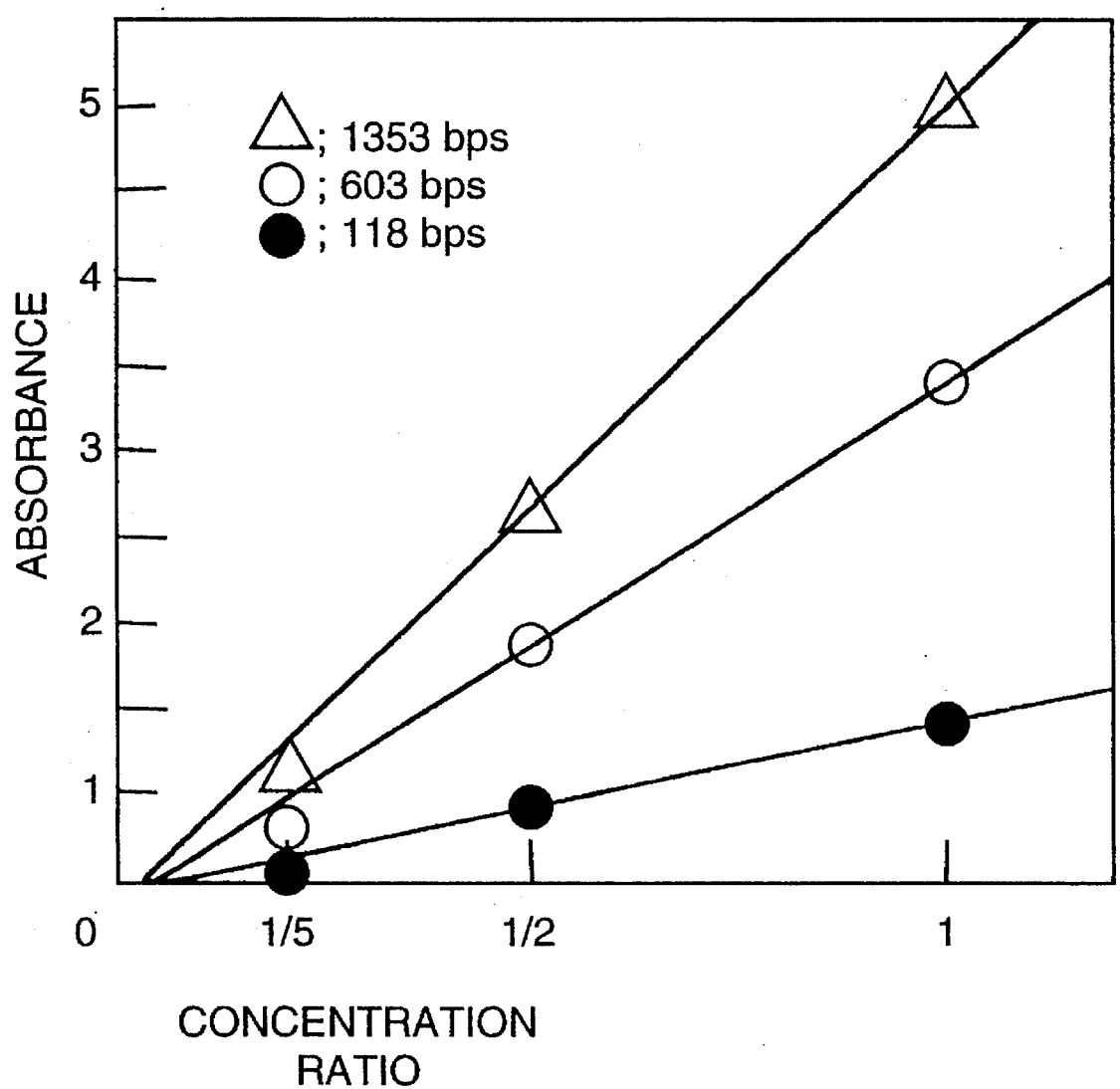
FIG. 17 is a graph showing the relationship between sample concentration and absorbance according to the present invention.

FIG. 17 shows the results of data provided under the foregoing conditions of Table 4. Even when the sample is diluted with distilled water, the measurement can be performed without any problem. Specifically, in FIG. 17, the abscissa indicates a concentration ratio (amount of sample/amount of sample+amount of distilled water), while the ordinate represents the absorbance. As FIG. 17 shows, by using the microinjector according to the present invention, absorbance data corresponding to the concentration ratio of the sample can be obtained.

Figure 18:
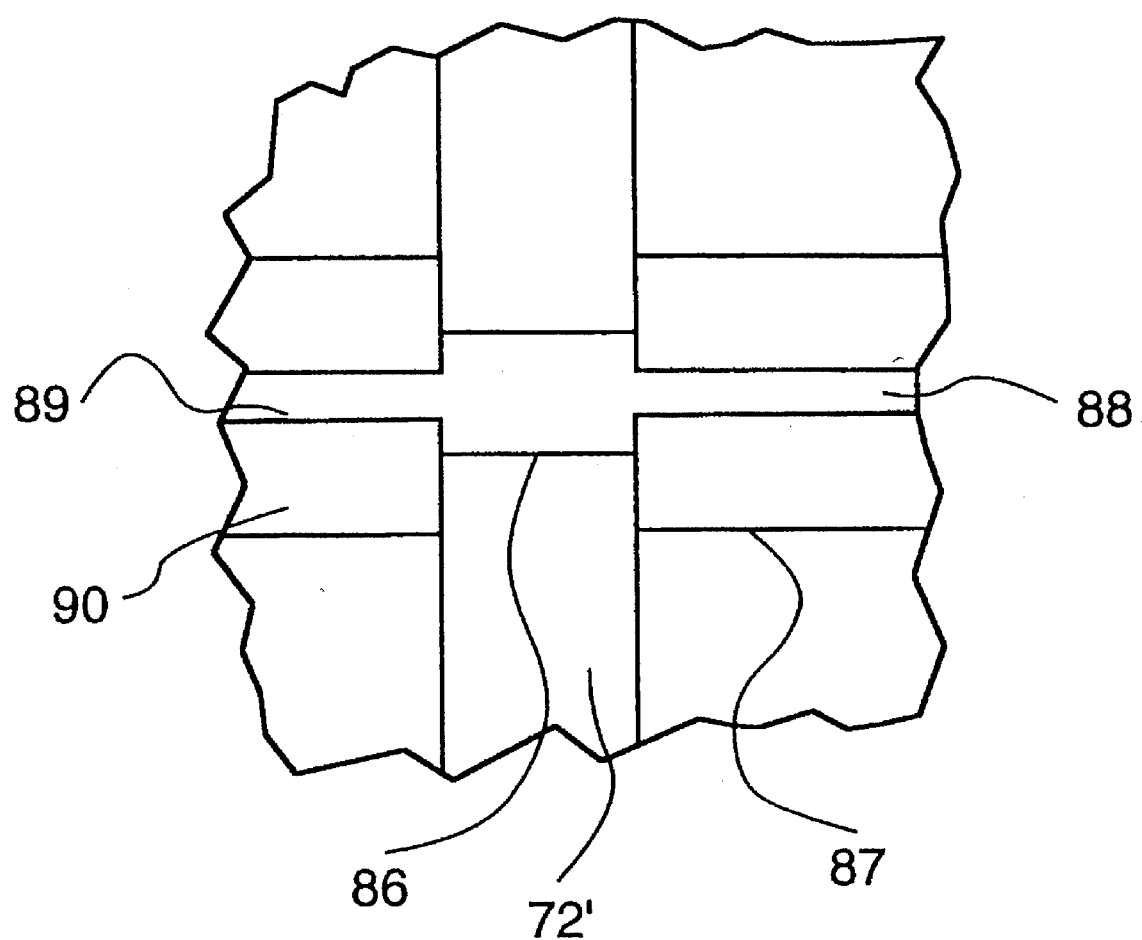
FIG. 18 is a schematic sectional view of a modified embodiment of the rotor shown in FIG. 14(a) taken along section line 2—2.

FIG. 18 shows a partial sectional view, schematically, taken along line 2—2 of FIG. 14(a) of a modified rotor 72', wherein the metering section 86 is provided with a diameter that is greater than the inner diameter 88 of capillary 87 and the diameter 89 of flow channel 90 so that slight misalignment following rotation thereof does not result in inadvertent flow blockage.

Although the invention has been disclosed with respect to the various embodiments, modifications and further embodiments are possible in accordance with the teachings presented in the specification and accompanying drawings.

We claim:

1. An apparatus for analyzing one of a virus, organism and a nucleic acid by disassociating a given region of double-stranded DNA molecules containing nucleic acids into single-strand DNAs complementary to each other, comprising:

means for electrophoresing the single-strand DNAs with a gel filled capillary and analyzing the sequence polymorphism of the DNA with the use of the higher order structures of the single strand DNAs specific for the sequence polymorphism;

said capillary having an inner diameter of 100 μm or less;

means for controlling the capillary temperature and means for independently controlling the sample temperature whereby the DNA sample is heated to a temperature higher than a disassociation temperature thereof for directly injecting the heated sample into the capillary and whereby the capillary temperature is controlled to be at a constant temperature.

2. An apparatus for analyzing according to claim 1, wherein said means for controlling the temperature of the capillary includes controller connected to a plurality of Peltier elements bonded to a plate for heat transfer support of the capillary.

\* \* \* \* \*